United States Patent
Walak

(10) Patent No.: US 8,382,739 B2
(45) Date of Patent: Feb. 26, 2013

(54) COMPOSITE MEDICAL DEVICE AND METHOD OF FORMING

(75) Inventor: Steven E. Walak, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2123 days.

(21) Appl. No.: 10/725,890

(22) Filed: Dec. 2, 2003

(65) Prior Publication Data
US 2005/0115624 A1  Jun. 2, 2005

(51) Int. Cl.
*A61M 25/00* (2006.01)
(52) U.S. Cl. .................................................. 604/525
(58) Field of Classification Search .......... 604/523–527; 172/169, 172
See application file for complete search history.

(56) References Cited

U.S. PATENT DOCUMENTS

| | | |
|---|---|---|
| 4,842,590 A | 6/1989 | Tanabe et al. |
| 5,001,825 A | 3/1991 | Halpern |
| 5,061,257 A | 10/1991 | Martinez et al. |
| 5,238,004 A | 8/1993 | Sahatjian et al. |
| 5,308,342 A | 5/1994 | Sepetka et al. |
| 5,397,306 A | 3/1995 | Nobuyoshi et al. |
| 5,437,632 A | 8/1995 | Engelson |
| 5,636,641 A | 6/1997 | Fariabi |
| 5,697,906 A | 12/1997 | Ariola et al. |
| 5,843,050 A * | 12/1998 | Jones et al. .................. 604/525 |
| 5,911,715 A | 6/1999 | Berg et al. |
| 6,019,736 A | 2/2000 | Avellanet et al. |

(Continued)

FOREIGN PATENT DOCUMENTS

| | | |
|---|---|---|
| JP | 2000254235 | 9/2000 |
| WO | WO 9958184 A1 * | 11/1999 |
| WO | WO 03/041783 | 5/2003 |

OTHER PUBLICATIONS

U.S. Appl. No. 10/346,698, filed Jan. 17, 2003, Art Miller et al.

*Primary Examiner* — Kevin C Sirmons
*Assistant Examiner* — Bradley Osinski
(74) *Attorney, Agent, or Firm* — Seager, Tufte & Wickhem, LLC

(57) ABSTRACT

Composite medical devices, such as catheters, or the like. In at least some embodiments, composite medical devices, and/or shafts for use therein, that can include a more flexible inner portion and a less flexible outer portion. In some embodiments, the composite elongate shaft can be constructed by forming a metallic outer portion including a first metallic material about a metallic inner portion including a second metallic material different from the first material. The second metallic material can be more flexible than the first metallic material. A segment of the metallic outer portion can then be removed from the composite shaft to expose a segment of the metallic inner portion. As portions of the outer portion are removed, and/or portions of the inner portion are exposed, certain characteristics along the length of the shaft can be achieved. For example, portions of the shaft can be rendered more flexible by the removal of the outer portion to expose the inner portion. Additionally, portions of the shaft can be maintained and/or rendered less flexible, or stiffer, by allowing the outer portion to remain thereon. As such, the composite elongate shaft can provide a shaft for a medical device that can include desired characteristics, such as flexibility, torqueability, or the like, along different portions of the shaft.

44 Claims, 3 Drawing Sheets

U.S. PATENT DOCUMENTS

| | | | |
|---|---|---|---|
| 6,039,699 A * | 3/2000 | Viera | 600/585 |
| 6,045,547 A * | 4/2000 | Ren et al. | 604/525 |
| 6,142,975 A | 11/2000 | Jalisi et al. | |
| 6,306,105 B1 * | 10/2001 | Rooney et al. | 600/585 |
| 6,340,441 B1 | 1/2002 | Meyer et al. | |
| 6,368,316 B1 | 4/2002 | Jansen et al. | |
| 6,387,060 B1 | 5/2002 | Jalisi | |
| 6,508,803 B1 | 1/2003 | Horikawa et al. | |
| 6,595,958 B1 | 7/2003 | Mickley | |
| 6,596,005 B1 | 7/2003 | Kanz et al. | |
| 6,610,930 B1 | 8/2003 | Seuntjens | |
| 2002/0007958 A1 | 1/2002 | Rivelli et al. | |

OTHER PUBLICATIONS

Nam et al., "Phase transformation behavior and wire drawing properties of Ti-Ni-Mo shape memory alloys," *J. Materials Sci.*, 36(17):4181-4188, 2001.

Miyazaki et al., "Recent Development in TiNi-based Shape Memory Alloys," Part of SPIE Conference on Smart Materials Technologies, *SPIE*, 3324:2-13, 1998.

Sakum et al., "Effect of Copper Content on Superelasticity Characteristics in Ti-Ni and Ti-Ni-Cu Alloy Wires," *Materials Transactions*, 43(5):828-833, 2002.

Siddons et al., "Tensile and compression performance of superelastic NiTi tubing," *Materials Science and Technology*, 17(9):1073-1078, Sep. 2001.

Yea-Yang Su, "The quest for wire surface quality for medical applications," Article from *Georgia Institute of Technology*, pp. 112-118.

S.K. Wu et al., "Wire drawing conducted in the R-phase of TiNi shape memory alloys," *Materials Letters*, 46:175-180, Nov. 2000.

Xu et al., "Fabrication of TiNi/CFRP smart composite using cold drawn TiNi wires," *Proc. SPIE*, vol. 4699:564-574, 2002.

Yoshida et al., "The drawability of Ni-Ti shape-memory alloy wires," *Wire*, 45(2):89-94, 1995.

* cited by examiner

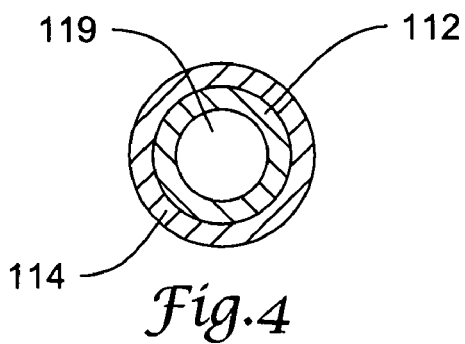
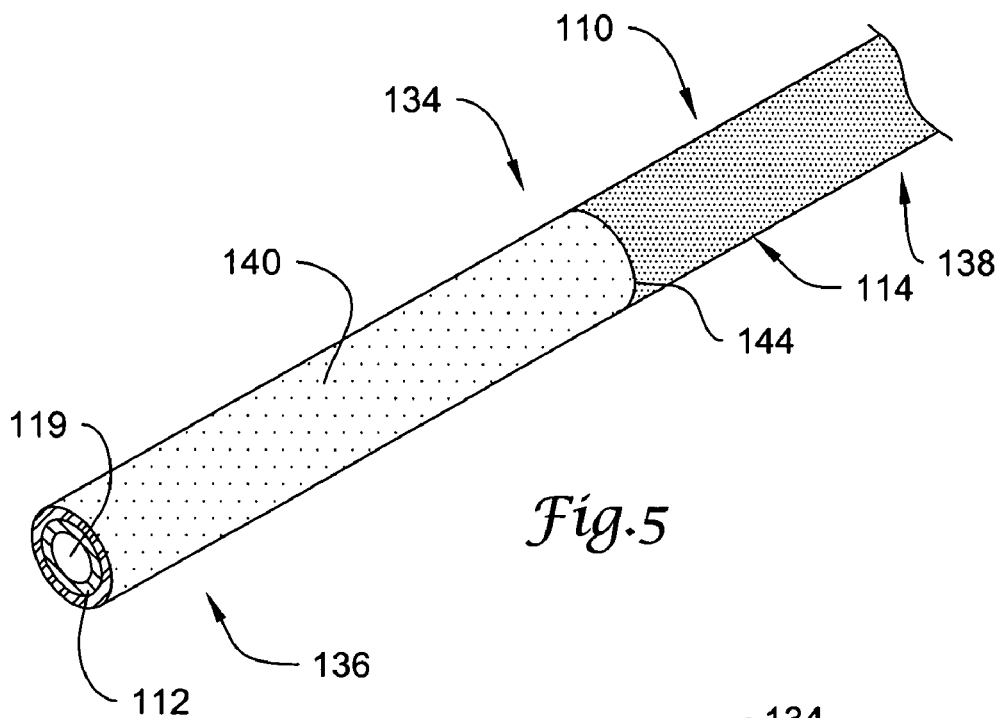
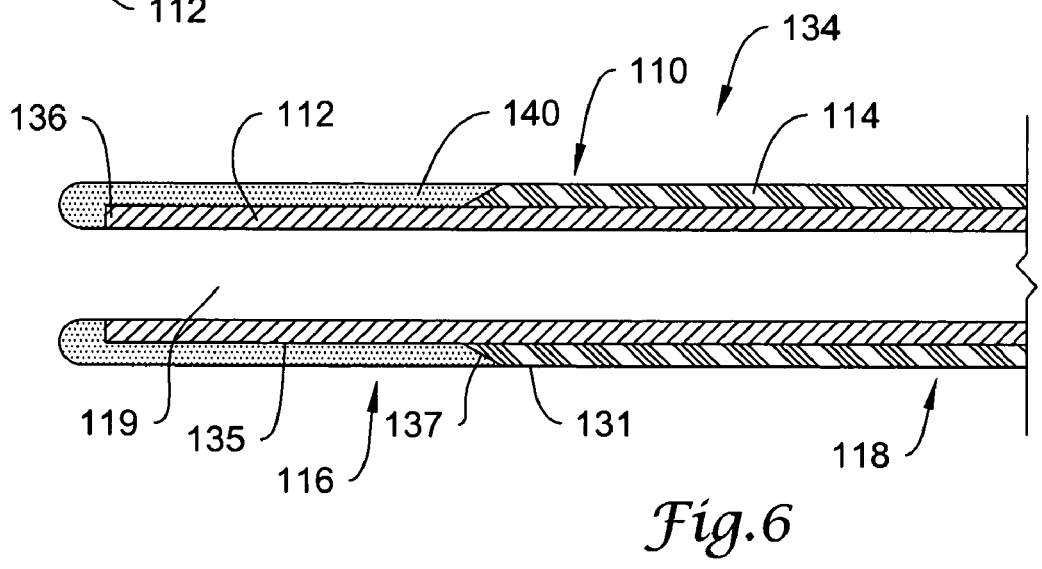

COMPOSITE MEDICAL DEVICE AND METHOD OF FORMING

FIELD

The invention relates generally to medical devices and more specifically to medical devices, such as catheters and the like, that include a composite shaft or other such structure.

BACKGROUND

A wide variety of medical devices have been developed for use in facilitating navigation and treatment throughout a patient's anatomy. For example, catheters are commonly used alone or in conjunction with other devices to facilitate navigation through and/or treatment within a patient's often tortuous anatomy, for example, through the vascular anatomy of a patient. It can be desirable to combine a number of performance features in such medical devices. For example, it can be desirable to have a relatively high level of pushability and torqueability at or near the proximal end of a device, while having flexibility at or near the distal end of the device to aid in navigation.

The prior art offers a number of different structures and assemblies for medical devices, and methods for making such structures, assemblies, and medical devices. Each of these different structures, assemblies and methods has certain advantages and disadvantages. However, there is an ongoing need to provide alternative structures and assemblies for medical devices, and methods for making such structures, assemblies, and medical devices, for example, to in aid in providing desirable performance features in such medical devices.

SUMMARY OF SOME EMBODIMENTS

The invention provides design, material, structural and manufacturing alternatives for composite medical devices. In some embodiments, the invention provides alternatives for composite medical devices that include a more flexible inner portion and a less flexible outer portion.

BRIEF DESCRIPTION OF THE FIGURES

The invention may be more completely understood in consideration of the following detailed description of various embodiments of the invention in connection with the accompanying drawings, in which:

FIG. 4 is a cross-sectional view of the tubular composite elongate shaft of FIG. 2, taken along the 4-4 line;

FIG. 5 is a perspective view of the tubular composite elongate shaft of FIG. 3 with the addition of a distal polymer sleeve; and FIG. 6 is a partial cross-sectional view of the shaft with sleeve of FIG. 5.

Figure 1:
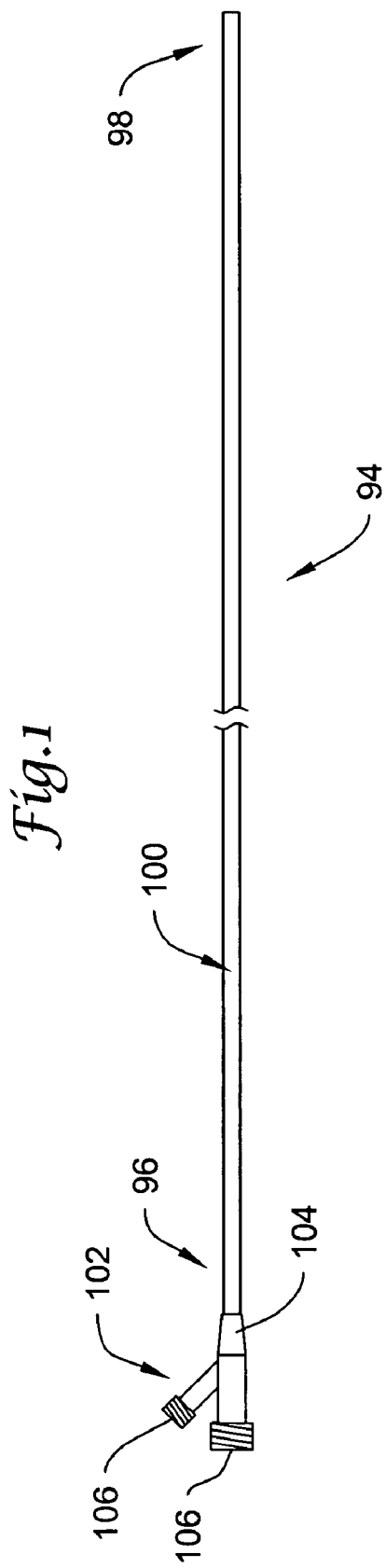
FIG. 1 is a plan view of a catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention. For example, although discussed with specific reference to infusion type catheters in the particular embodiments described herein, the invention may be applicable to a variety of medical devices that are adapted to be advanced into the anatomy of a patient through an opening or lumen. For example, certain aspects of the invention may be applicable to fixed wire devices, other catheters (e.g. balloon, stent delivery, etc.) drive shafts for rotational devices such as atherectomy catheters and IVUS catheters, endoscopic devices, laproscopic devices, embolic protection devices, spinal or cranial navigational or therapeutic devices, and other such devices. Many such devices may include a shaft construction, and/or certain other aspects of the invention as disclosed herein.

In at least some embodiments, the invention is directed to composite medical devices, and/or shafts for use therein, that can include a more flexible inner portion and a less flexible outer portion. The composite shaft can have two portions, and/or layers of material, an inner more flexible portion, and an outer, stiffer portion. In some embodiments, both the inner member and the outer member can be formed of metals or metal alloys as described herein. In some embodiments, the composite elongate shaft can be constructed by forming a metallic outer portion including a first metallic material about a metallic inner portion including a second metallic material different from the first material. The second metallic material can be more flexible than the first metallic material. A segment of the metallic outer portion can then be removed from the composite shaft to expose a segment of the metallic inner portion. As portions of the outer portion are removed, and/or portions of the inner portion are exposed, certain characteristics along the length of the shaft can be achieved. For example, portions of the shaft can be rendered more flexible by the removal of the outer portion to expose the inner portion. Additionally, portions of the shaft can be maintained and/or rendered less flexible, or stiffer by allowing the outer portion to remain thereon. As such, the composite elongate shaft can provide a shaft for a medical device that can include desired characteristics, such as flexibility, torqueability, or the like, along different portions of the shaft.

The concept of a composite elongate shaft including a more flexible inner portion, and a more stiff outer portion can be used in a broad variety of structures for use as medical devices. For example, the composite elongate shaft may be a tubular member having an inner portion made of a more flexible material, and an outer portion made of a stiffer material. The tubular shaft could be treated and/or worked to remove portions of the outer material and/or expose portions of the inner material to provide different characteristics, such as flexibility or stiffness characteristics, along the length of the shaft. For example, such a construction can be used as a shaft for a medical device such as a catheter, or the like.

For example, refer now to FIG. 1, which illustrates a sectional side view of a catheter 94 that has a catheter body 100 having a proximal end 96 and a distal end 98. The catheter 94 may include some conventional structures, such as a manifold 102 positioned adjacent the proximal end 96 and connected to the catheter body 100 and a strain relief 104. The manifold 102 generally contains ports 106 that allow for fluid-tight connections with one or more lumens within the catheter 94.

Figure 2:
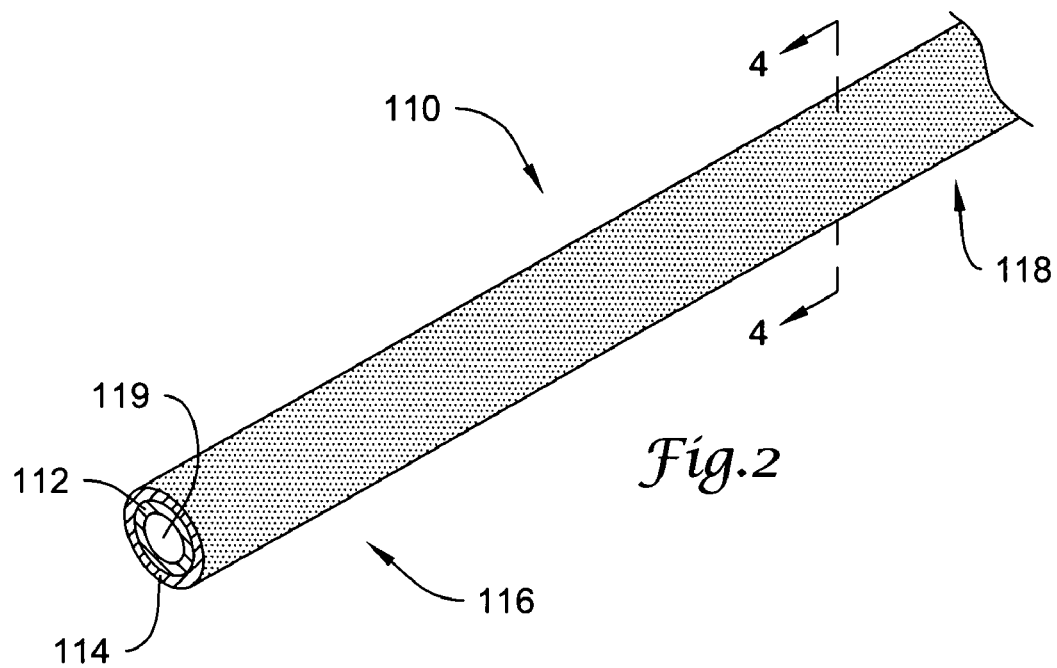
FIG. 2 is a schematic perspective view of a distal portion of a tubular composite elongate shaft, prior to processing to remove a part of the outer portion.

Refer now to FIG. 2, which illustrates a composite elongate shaft 110 that can be adapted and/or configured for use in a medical device, for example, as part of the body 100 of the catheter 94 or the like. The composite elongate shaft 110 has an inner portion 112 and an outer portion 114 disposed about the inner portion 112. The elongate shaft 110 has a distal region 116 and a proximal region 118. The inner portion 112 defines at least one lumen 119 that extends from the distal region 116 to the proximal region 118 of the shaft 110. FIG. 4 illustrates a cross-sectional view of the proximal portion of the shaft 110, including the inner and outer portions 112/114 and showing the lumen 119. Referring back to FIG. 2, the composite elongate tubular shaft 110 is adapted and/or configured such that the inner portion 112 is more flexible than the outer portion 114. This can be achieved, for example, through structural design or material selection used to create the inner portion 112 and the outer portion 114. In this regard, the composite elongate shaft 110 can be formed, and thereafter worked, for example, to remove portions of the outer portion 114 and/or expose portions of the inner portion 112 to provide different characteristics, such as flexibility or stiffness characteristics, along the length of the shaft 110. As such, through such additional working, the composite elongate shaft 110 in some embodiments can provide a shaft for a medical device, such as a catheter, that can include desired characteristics, such as flexibility, torqueability, or the like, along different portions of the shaft 110, as will be discussed in more detail below.

In at least some embodiments, the inner portion 112 and/or the outer portion 114 of the composite elongate shaft 110 can be made of any suitable materials, as long as the desired flexibility aspects of each portion is appropriate. For example, the inner portion 112 and/or the outer portion 114 can each individually include metals, metal alloys, polymers, elastomers, such as high performance polymers, or the like, or combinations or mixtures thereof.

Some examples of suitable metals and metal alloys include stainless steel, such as 304V, 304L, and 316L stainless steel; nickel-titanium alloy, such as linear elastic or superelastic (i.e., pseudoelastic) nitinol; nickel-chromium alloy, nickel-chromium-iron alloy, cobalt alloy, tungsten, tungsten alloy, tantalum or tantalum alloys, gold or gold alloys, platinum or platinum alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), Elgiloy, hastelloy; monel 400; inconel 625; refractory metals, or the like; or other suitable material, or combinations or alloys thereof.

The word nitinol was coined by a group of researchers at the United States Naval Ordinance Laboratory (NOL) who were the first to observe the shape memory behavior of this material. The word nitinol is an acronym including the chemical symbol for nickel (Ni), the chemical symbol for titanium (Ti), and an acronym identifying the Naval Ordinance Laboratory (NOL). In some embodiments, nitinol alloys can include in the range of about 50 to about 60 weight percent nickel, with the remainder being essentially titanium. It should be understood, however, that in other embodiment, the range of weight percent nickel and titanium, and or other trace elements may vary from these ranges. Within the family of commercially available nitinol alloys, are categories designated as "superelastic" (i.e. pseudoelastic) and "linear elastic" which, although similar in chemistry, exhibits distinct and useful mechanical properties.

In some embodiments, a superelastic alloy, for example a superelastic nitinol can be used to achieve desired properties. Such alloys typically display a substantial "superelastic plateau" or "flag region" in its stress/strain curve. Such alloys can be desirable in some embodiments because a suitable superelastic alloy can provide a structure that exhibits some enhanced ability, relative to some other non-superelastic materials, of substantially recovering its shape without significant plastic deformation, upon the application and release of stress, for example, during insertion or navigation of the guidewire in the body.

In some other embodiments, a linear elastic alloy, for example a linear elastic nitinol can be used to achieve desired properties. For example, in some embodiments, certain linear elastic nitinol alloys can be generated by the application of cold work, directional stress, and heat treatment, such that the material fabricated does not display a substantial "superelastic plateau" or "flag region" in its stress/strain curve. Instead, in such embodiments, as recoverable strain increases, the stress continues to increase in a somewhat linear relationship until plastic deformation begins. In some embodiments, the linear elastic nickel-titanium alloy is an alloy that does not show any martensite/austenite phase changes that are detectable by DSC and DMTA analysis over a large temperature range. For example, in some embodiments, there is no martensite/austenite phase changes detectable by DSC and DMTA analysis in the range of about −60° C. to about 120° C., and in other embodiments, in the range of about −100° C. to about 100° C. The mechanical bending properties of such material are therefore generally inert to the effect of temperature over a broad range of temperature. In some particular embodiments, the mechanical properties of the alloy at ambient or room temperature are substantially the same as the mechanical properties at body temperature. In some embodiments, the use of the linear elastic nickel-titanium alloy allows a structure to exhibit superior "pushability" around tortuous anatomy. One example of a suitable nickel-titanium alloy exhibiting at least some linear elastic properties is FHP-NT alloy commercially available from Furukawa Techno Material Co. of Kanagawa, Japan. Additionally, some examples of suitable nickel-titanium alloy exhibiting at least some linear elastic properties include those disclosed in U.S. Pat. Nos. 5,238,004 and 6,508,803, which are incorporated herein by reference.

In at least some embodiments, the inner portion 112 and the outer portion 114 are formed of different materials, for example materials having different moduli of elasticity, resulting in a difference in flexibility between the two portions 112/114. For example, the material used to construct the outer portion 114 can be relatively stiff to enhance certain characteristics, such as pushability and/or torqueability. Likewise, the material used to construct the inner portion 112 can be relatively flexible by comparison to enhance certain characteristics, such as lateral trackability and steerability. In some embodiments, the outer portion 114 can include a material having a relatively high elastic modulus and high yield strength, while the inner portion 112 is formed of a relatively more flexible material. In some embodiments, both the inner portion 112 and the outer portion 114 are formed of metallic materials. For example, the outer portion 114 can be formed of a relatively stiff metallic material, such as stainless steel, MP35N, tantalum, tungsten, or other suitable relatively stiff elastic/plastic metallic material, and the inner portion 112 can be formed of a relatively flexible metallic material, such as a super elastic (pseudoelastic) or linear elastic alloy, for example a super elastic or linear elastic nickel-titanium alloy such as Nitinol.

In at least some embodiments, portions or all of the elongate shaft 110 and/or portions of the inner and/or outer portions 112/114, may be doped with, made of, coated or plated with, or otherwise include a radiopaque material. Radiopaque materials are understood to be materials capable of producing a relatively bright image on a fluoroscopy screen or another imaging technique during a medical procedure. This relatively bright image aids the user of a device incorporating the elongate shaft 110 in determining its location. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted into the elongate shaft 110. For example, to enhance compatibility with Magnetic Resonance Imaging (MRI) machines, it may be desirable to make the elongate shaft 110, or other portions of a medical device into which it is incorporated, in a manner that would impart a degree of MRI compatibility. For example, the elongate shaft 110, or portions thereof, may be made of a material that does not substantially distort the image and create substantial artifacts (artifacts are gaps in the image). Certain ferromagnetic materials, for example, may not be suitable because they may create artifacts in an MRI image. The elongate shaft 110, or portions thereof, may also be made from a material that the MRI machine can image. Some materials that exhibit these characteristics include, for example, tungsten, Elgiloy, MP35N, nitinol, and the like, and others.

The composite elongate shaft 110 can have a tubular or a hollow cross-section, as shown, or can include a combination of areas having solid cross-sections and hollow cross sections. Moreover, elongate shaft 110, or portions thereof, and/or the lumen 119 defined thereby, can have various cross-sectional geometries, depending greatly upon the desired characteristics. The cross-sectional geometries along the length of the elongate shaft 110 can also be constant or can vary. For example, FIG. 2 depicts the elongate shaft 110 and the lumen 119 as having generally round cross-sectional shapes. It can be appreciated that other cross-sectional shapes or combinations of shapes may be utilized without departing from the spirit of the invention. For example, the cross-sectional shape of elongate shaft 110 and/or lumen 119 may be oval, rectangular, square, polygonal, and the like, or any suitable shape.

The elongate shaft 110 can be formed in several different ways. For example, the inner portion 112 and the outer sleeve 114 can be co-drawn, co-extruded or otherwise processed, for example, over a mandrel or other such structure or device to form the elongate shaft 110 in which the outer portion 114 is of unitary construction with the inner portion 112. In some embodiments, such unitary construction allows the formation of a composite shaft 110 that can be co-drawn and straightened such that the inner portion 112 and the outer portion 114 are formed together as one unitary construction. In other embodiments, the inner portion 112 and the outer portion 114 may be separately manufactured, and thereafter, the outer portion 114 can be disposed about and securely connected to inner portion 112. Some examples of suitable attachment techniques can include, soldering, welding, adhesive bonding, heat bonding or shrinking techniques, mechanical bonding or fitting, heat crimping, or the like, or combinations thereof.

Once formed, the composite elongated shaft 110 may be further processed, for example, to remove portions of the outer portion 114 and/or expose portions of the inner portion 112. As portions of the outer portion 114 are removed, and/or portions of the inner portion 112 are exposed, certain characteristics along the length of the shaft 110 can be achieved. For example, portions of the shaft 110 where the outer portion 114 has been partially, or totally removed to expose the inner portion 112, will have more of the flexibility characteristics of the more flexible material of the inner portion 112, and less of the flexibility characteristics of the stiffer outer portion 114. Additionally, portions of the shaft 110 that still include the outer portion 114 disposed thereon will retain the stiffer flexibility characteristics of the material of the outer portion 114. As such, the composite elongate shaft 110 can provide a tubular shaft for a medical device that can include desired characteristics, such as flexibility, torqueability, or the like, along different portions of the shaft 110.

Figure 3:
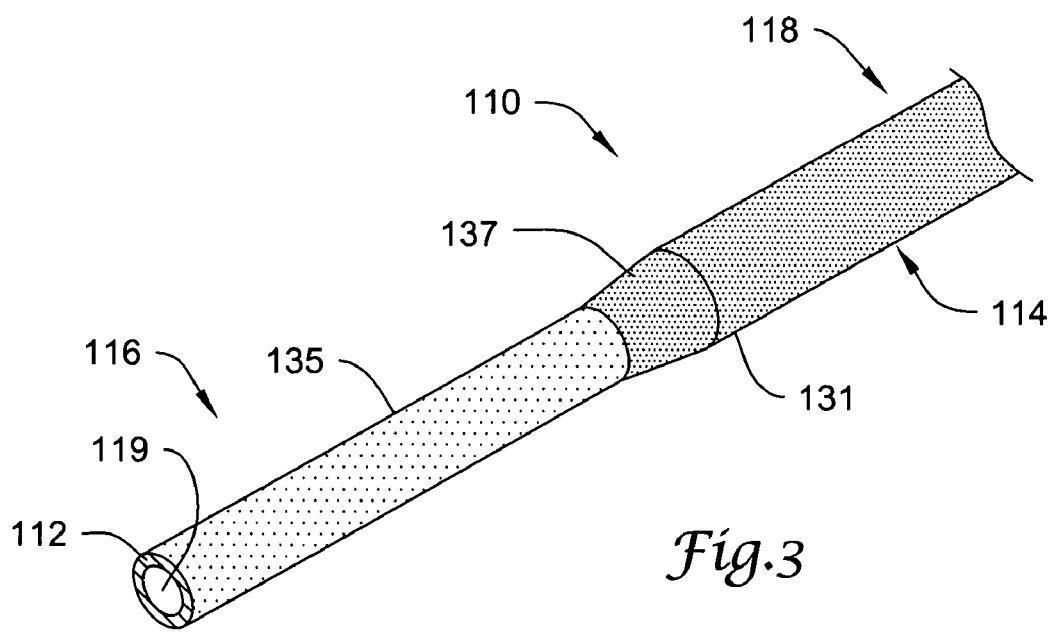
FIG. 3 is a schematic perspective view of the tubular composite elongate shaft of FIG. 2, after processing to remove a part of the outer portion.

For example, refer now to FIG. 3, which illustrates the composite elongated shaft 110 of FIG. 2, wherein a part of the outer portion 114 has been removed from the elongated shaft 110 to expose a part of the inner portion 112. In this embodiment, the outer portion 114 has been removed from a portion of the distal region 116 of the elongated shaft 110. The removal of the outer portion 114 exposes the more flexible inner portion 112, and as such, provides the distal region 116 with greater flexibility due to the removal of the stiffer material of the outer portion 114. Additionally, the outer portion 114 of stiffer material remains on the proximal region 118 of the shaft, and therefore provides the proximal region 118 with greater stiffness. As such, the elongated shaft 110 can provide a tubular structure that may be used, for example, as a body for a medical device, such as a catheter, that has a relatively high level of stiffness for pushability and torqueability at or near the proximal region 118, and has a relatively high level of flexibility at or near the distal region 116, which may be desirable, for example, to aid in navigation of the device.

It should be understood, however, that in other embodiments, the outer portion 114 can been removed from other regions, or multiple regions, along the length of the elongated shaft 110 to provide for varying characteristics along the length of the shaft 110. For example, the outer portion 114 could be removed from an intermediate or proximal region along the length of the shaft 110 to provide such regions with desired characteristics, such as enhanced flexibility characteristics. Additionally, the outer portion 114 may be selectively removed to form portions of the elongated shaft including discrete sections where the outer portion 114 has been removed and discrete sections where the outer portion remains. For example, in some embodiments, parts of the outer portion 114 may be removed to form a constant or varying pattern on the surface of a part of the elongated shaft where a portion of the outer portion 114 has been removed. In some embodiments, the pattern may include, for example, a spiral or helical shape, or one or more or a series of cells, squares, circles, ovals, rectangles, triangles, and/or other shapes or arrangements where the parts of the outer portion 114 have been removes, while adjacent parts of the outer portion 114 remain. The thickness of the remaining material and/or the size, shape, density, pattern, and/or pitch of the pattern can also vary, for example, to provide for desired characteristics, such as stiffness and/or flexibility characteristics. For example, in some embodiments, the selective removal of parts of the outer portion 114 can provide for a gradual and/or controlled transition in stiffness and/or flexibility characteristics.

Removal of the outer portion 114 from the elongated shaft 110 to expose the inner portion 112 may be achieved in any of a broad variety of ways, depending somewhat upon the material used, and the desired finish to the shaft 110. In some embodiments, the outer portion 114 can be removed, for example, through mechanical processes, such as grinding, for example centerless grinding, abrasion, stripping or other such techniques, or the like. Some centerless grinding techniques may utilize an indexing system employing sensors (e.g., optical/reflective, magnetic) to avoid excessive grinding of the shaft 110. In addition, the centerless grinding technique may utilize a CBN or diamond abrasive grinding wheel that is well shaped and dressed to avoid grabbing the shaft 110 during the grinding process. In some embodiments, the shaft 110 can be centerless ground using a Royal Master HI-AC centerless grinder. Some examples of suitable grinding methods are disclosed in U.S. patent application Ser. No. 10/346,698 entitled "IMPROVED STRAIGHTENING AND CENTERLESS GRINDING OF WIRE FOR USE WITH MEDICAL DEVICES" filed Jan. 17, 2003, which is herein incorporated by reference. In some other embodiments, the outer portion 114 can be removed, for example, through chemical processes, for example, chemical etching, or the like.

Additionally, either during or after removal of the outer portion 114 from the elongated shaft 110 to expose the inner portion 112, one or more tapers, tapered regions and/or reduced diameter portions can be formed in the shaft 110, for example in the distal region 116 as shown. In some embodiments distal region 116 may be tapered and have an initial outside size or diameter that can be substantially the same as the outside diameter of proximal region 118, which then tapers to a reduced size or diameter. The tapered regions may be linearly tapered, tapered in a curvilinear fashion, uniformly tapered, non-uniformly tapered, or tapered in a stepwise fashion. The angle of any such tapers can vary, depending upon the desired flexibility characteristics. The length of the taper may be selected to obtain a more (longer length) or less (shorter length) gradual transition in stiffness, due to either or both the removal of the material of the outer portion 114 and/or to the reduction in diameter, or both.

The tapers and/or reduced diameter portions may be formed in the material of the outer portion 114, the material of the inner portion 112, or both, as desired. Additionally, the tapers and/or reduced diameter portions can be formed in conjunction with the removal of the outer portion 114 to expose the inner portion 112. For example, in the embodiment shown, a process, such as a centerless grinding process, can be used to both remove a section of the outer portion 114 from the distal region 116, and can be used to create tapers and/or reduced diameter portions in either/or both the outer portion 114, and the inner portion 112.

In the embodiment shown in FIG. 3, the distal region 116 includes two constant diameter regions 131 and 135, interconnected by one tapering region 137. The constant diameter regions 131 and 135 and tapering region 137 are disposed such that the distal region 116 includes a geometry that decreases in cross sectional area toward the distal end thereof. Additionally, it can be noted that the tapering region 137 and the constant diameter region 131 are defined in the outer surface of the outer portion 114, while the constant diameter region 135 is defined in the outer surface of the inner portion 112. In some embodiments, these constant diameter and tapering regions 131, 135 and 137 are adapted and configured to obtain a transition in stiffness, and provide a desired flexibility characteristic. Additionally, in some embodiments, the tapering can provide for a smooth transition between portions still including material of the outer portion 114, and portions where the material of the outer portion 114 has been removed to expose the material of the inner portion 112. For example, as illustrated in FIG. 3, the taper portion 137 can represent a profile over which the outer portion 114 is substantially or completely intact at the proximal end of the taper portion 137, and is substantially or completely missing at the distal end of the same taper portion 137. Therefore, in some respects, the taper portion 137 can represent a transition between the outer portion 114 being intact and the outer portion 114 being absent. Furthermore, the constant diameter portion 135 can represent a profile over which the outer portion 114 is substantially or completely missing, thereby exposing the inner core 112. Similarly, the constant diameter portion 135 can represent a profile over which portions of the inner core 112 may and/or may not have been removed to form a desired profile.

Although FIG. 3 depicts distal region 116 of the elongated shaft 110 as being tapered and/or having parts of the outer portion 114 removed, it can be appreciated that essentially any portion of the elongated shaft 110 may be tapered and the taper can be in either the proximal and/or the distal direction, and/or may have parts of the outer portion 114 removed. As shown in FIG. 3, the tapered region may include one or more portions where the outside diameter is narrowing, and portions where the outside diameter remains essentially constant. The number, arrangement, size, and length of the narrowing and constant diameter portions can be varied to achieve the desired characteristics, such as flexibility and torque transmission characteristics. The narrowing and constant diameter portions as shown in FIG. 3 are not intended to be limiting, and alterations of this arrangement can be made without departing from the spirit of the invention. The tapered and constant diameter portions of the tapered region may be formed by any one of a number of different techniques, for example, those discussed above with regard to removal of the outer portion 114, or other techniques.

It will be understood that a broad variety of materials, dimensions, and structures can be used to construct suitable embodiments, depending upon the desired characteristics. The following dimensions are included by way of example only, and are not intended to be limiting. In at least some embodiments, the length of shaft member 110, and/or the length of individual regions thereof, are typically dictated by the length and flexibility characteristics desired in the final medical device. For example, proximal region 116 may have a length in the range of about 5 to about 300 centimeters or more, distal region 118 may have a length in the range of about 5 to about 200 centimeters or more, and the shaft 110 may have a total length in the range of about 10 to about 400 centimeters or more. It can be appreciated that alterations in these lengths can be made without departing from the spirit of the invention.

Likewise, the width and/or diameter of the shaft member 110, or individual portions thereof, and the lumen 119, are also typically dictated by the characteristics desired in the final medical device. For example, in some embodiments, the shaft 110, for example about the proximal region 118, can have an outer diameter in the range of about 0.1 to about 6 millimeters, or more, or in the range of about 0.13 to about 5.1 millimeters or more. In some embodiments, the inner portion 112 can have an inner portion thickness in the range of about 0.1 to about 5.5 millimeters, or in the range of about 0.12 to about 5 millimeters or more, and an inner diameter defining the lumen 119 in the range of about 0.05 to about 5.5 millimeters, or in the range of about 0.07 to about 5.0 millimeters or more. The outer portion 114 can have a thickness in the range of about 0.1 to about 5.5 millimeters or more, or in the range of about 0.12 to about 5 millimeters or more.

After the shaft 110 is formed and worked, as shown in FIG. 3, the result is a composite elongate tubular shaft 110 that includes a distal region 116 with greater flexibility due to the removal of the stiffer material of the outer portion 114, and a proximal region 118 with greater stiffness due to the presence of the stiffer material of the outer portion 114. The shaft 110 may be used "as is" in some applications, or may be provided with a coating, or may be combined with other structures for use as a catheter, or other medical device. For example, other structures such as a polymer tip, a spring tip or a combination of a spring/polymer tip construction may be added and/or combined with the shaft 110 to form a catheter, or other medical device. Additionally, other structures such as additional coils, braids, radiopaque members, such as coils or bands, a manifold, coatings and/or surface treatment (e.g. lubricious, protective, biocompatibility, bioactive, or the like coatings and/or surface treatment) or the like, or many other such structures may be added and/or combined with the shaft 110 to form a catheter, for example catheter 94, or other medical device. Some examples of suitable catheter constructions including many of such structures, and others, are disclosed in U.S. Pat. Nos. 6,596,005; 6,595,958; 6,368,316; 5,697,906; 5,308,342; and 5,437,632, all of which are incorporated herein by reference.

For example, one embodiment of a catheter construction 134 incorporating the shaft 110 as a body of the catheter is illustrated in FIGS. 5 and 6 (which may, for example be used with catheter 94). The composite elongate tubular shaft 110 includes similar materials and structure as the shaft 110 described above with reference to FIG. 3, wherein like reference numbers indicate similar structure. In this embodiment, a polymer sleeve 140 is disposed over a portion of the distal region 116 of the shaft 110 to form a polymer tip. In the embodiment shown, the polymer sleeve 140 extends over portions of the distal region 116 of the shaft 110 where part or all of the outer portion 114 has been removed. For example, the polymer sleeve 140 extends from a location adjacent the constant diameter region 131 and extends over the tapering region 137 and the constant diameter region 135 of the shaft 110 to a location adjacent, and in some embodiments, extending distally of the distal end 136 of the shaft 110. In the embodiment shown, the polymer sleeve 140 can have an outer diameter that is substantially similar to that of the constant diameter region 131, for example, to provide for a catheter body having a somewhat uniform outer diameter along the length thereof.

The polymer sleeve 140 can be made from a variety of different polymers, and may be attached to the shaft in any suitable manner. For example, some suitable material for use as the outer sleeve 140 may include any material that would give the desired strength, flexibility or other desired characteristics. Examples of suitable polymer material may include any of a broad variety of polymers generally known for use as medical devices. The use of a polymer for outer sleeve 140 can serve several functions. The use of a polymer sleeve can improve the flexibility properties of the distal region 116. Choice of polymers for the sleeve 140 will vary the flexibility. For example, polymers with a low durometer or hardness will make a very flexible or floppy tip. Conversely, polymers with a high durometer will make a tip which is stiffer. In some embodiment, the sleeve 140 may include different sections having different polymers with different flexability characteristics to provide a transition in stiffness along the length of the sleeve 140. The use of polymers for the sleeve can also provide a more atraumatic tip for the catheter. An atraumatic tip is better suited for passing through fragile body passages. Finally, a polymer can act as a binder for radiopaque materials.

In some embodiments, the polymer material used is a thermoplastic polymer material. Some examples of some suitable materials include polyurethane, elastomeric polyamides, block polyamide/ethers (such as Pebax), silicones, and co-polymers. The sleeve may be a single polymer, multiple layers, or a blend of polymers. However, it should be understood that any of a broad variety of others may be used.

The sleeve 140 can be disposed around and attached to the shaft 110 using any suitable technique for the particular material used. In some embodiments, the sleeve 140 is attached by heating a sleeve of polymer material to a temperature until it is reformed around the distal shaft region 116, and/or any other structure in the distal region of the catheter. In some other embodiments, the sleeve 140 can be attached using other suitable attachment techniques, such as heat shrinking, mechanical bonding, adhesive bonding, welding, soldering, or the like. The sleeve 140 may be finished, for example, by a centerless grinding or other method, to provide the desired diameter and to provide a smooth and/or outer textured surface.

In each of the embodiments discussed above and in other medical device construction, part or all of the structures can be coated with or include a coating or surface treatment, for example a lubricious (e.g., hydrophilic), protective, biocompatible, bioactive, and/or other type of coating or surface treatment. Hydrophobic coatings such as fluoropolymers provide a dry lubricity that can improve handling and device exchanges. An example of a suitable fluoropolymer is polytetrafluoroethylene (PTFE), better known as TEFLON®. Lubricious coatings can improve steerability and improve lesion crossing capability. Examples of suitable lubricious polymers include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers can be blended among themselves or with formulated amounts of water insoluble compounds (including some polymers) to yield coatings with suitable lubricity, bonding, and solubility. In some embodiments, a distal portion of a medical device can be coated with a hydrophilic polymer as discussed above while the more proximal portions can be coated with a fluoropolymer.

In each of the embodiments discussed above, the elongated shaft 110 can be incorporated into the structure of a medical device, such as a catheter 94, and may provide a core structure that has a relatively high level of stiffness for pushability and torqueability at or near the proximal region 118, and has a relatively high level of flexibility at or near the distal region 116. Such properties are often desirable, for example, to aid in navigation of the device into which the shaft 110 can be incorporated.

It should also be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

I claim:

1. A composite medical device produced by a process comprising:

constructing a metallic composite elongate shaft by co-drawing or co-extruding a metallic outer portion comprising a first metallic material about a metallic inner portion including a lumen therein, the metallic inner portion comprising a second metallic material different from the first material, wherein the second metallic material is more flexible than the first metallic material, and wherein the composite elongate shaft has a distal region and a proximal region;

wherein co-drawing or co-extruding the metallic outer portion about the metallic inner portion forms the composite elongate shaft as a unitary construction; and removing a segment of the metallic outer portion from the composite shaft to expose a segment of the metallic inner portion.

2. The composite medical device of claim 1, wherein removing the segment of the metallic outer portion from the composite shaft to expose the segment of the metallic inner portion includes removing the segment of the metallic outer portion from the composite shaft in the distal region of the composite elongate shaft.

3. The composite medical device of claim 1, also including allowing a second segment of the metallic outer portion of the composite shaft to remain disposed about a second segment of the inner portion of the composite shaft.

4. The composite medical device of claim 3, wherein allowing the second segment of the metallic outer portion of the composite shaft to remain disposed about the second segment of the inner portion of the composite shaft includes allowing the second segment of the metallic outer portion of the composite shaft to remain disposed about the second segment of the inner portion in the proximal region of the composite elongate shaft.

5. The composite medical device of claim 1, wherein the segment of the metallic outer portion removed from the distal region of the shaft to expose the segment of the metallic inner portion, and also including allowing a second segment of the metallic outer portion of the composite shaft to remain disposed about a second segment of the inner portion at the distal region of the shaft.

6. The composite medical device of claim 1, wherein constructing the composite elongate shaft comprises co-drawing the metallic inner portion with the metallic outer portion to form the composite shaft.

7. The composite medical device of claim 1, wherein constructing the composite elongate shaft comprises co-extruding the metallic inner portion with the metallic outer portion to form the composite shaft.

8. The composite medical device of claim 1, wherein removing a segment of the metallic outer portion includes providing a tapered transition between a region in which the metallic outer portion is intact and a region in which the metallic outer portion has been removed.

9. The composite medical device of claim 1, wherein removing a segment of the metallic outer portion comprises grinding a segment of the metallic outer portion from the composite shaft to expose a segment of the metallic inner portion.

10. The composite medical device of claim 1, wherein removing a segment of the metallic outer portion comprises etching a segment of the metallic outer portion from the composite shaft to expose a segment of the metallic inner portion.

11. The composite medical device of claim 1, wherein the metallic inner portion comprises a nickel-titanium alloy.

12. The composite medical device of claim 1, wherein the metallic inner portion comprises beta titanium.

13. The composite medical device of claim 12, wherein the metallic outer portion comprises stainless steel, cobalt alloy, Elgiloy, MP35N, tantalum, tungsten, or refractory metal.

14. The composite medical device of claim 1, wherein the metallic inner portion comprises a super-elastic nickel-titanium alloy.

15. The composite medical device of claim 1, wherein the metallic inner portion comprises a linear-elastic nickel-titanium alloy.

16. The composite medical device of claim 1, wherein the metallic inner portion comprises a hollow tube having a length, and the lumen extends along the entire length.

17. The composite medical device of claim 1, wherein the metallic outer portion comprises stainless steel, cobalt alloy, Elgiloy, MP35N, tantalum, tungsten, or refractory metal.

18. The composite medical device of claim 1, wherein the composite medical device comprises a catheter.

19. The composite medical device of claim 1, wherein the composite medical device comprises a guide catheter.

20. The composite medical device of claim 1, wherein removing a segment of the metallic outer portion comprises grinding a segment of the metallic outer portion from a segment of the metallic inner portion, and the process further includes grinding a segment of the metallic inner portion to form a reduced outer diameter region on the metallic inner portion.

21. The composite medical device of claim 20, wherein the reduced diameter region of the metallic inner portion comprises a tapered portion.

22. The composite medical device of claim 1, wherein removing the segment of the metallic outer portion includes selectively removing part of the first metallic material to form a pattern of the first metallic material that remains on the shaft.

23. The composite medical device of claim 1, wherein the composite medical device comprises a hypo-tube catheter, a drug delivery catheter, a therapeutic catheter, a diagnostic catheter or a guide catheter.

24. The composite medical device of claim 1, wherein the metallic material of the inner portion has a modulus of elasticity that is less than the modulus of elasticity of the metallic material of the outer portion.

25. The composite medical device of claim 1, wherein the metallic material of the outer portion has higher tortional rigidity than the metallic material of the inner portion.

26. The composite medical device of claim 1 wherein the step of constructing a composite elongate shaft forms a composite elongate shaft of unitary construction having a bond along the entire length common to both the metallic inner portion and the metallic outer portion.

27. The composite medical device of claim 1 wherein during the step of constructing a composite elongate shaft a bond forms between the metallic inner portion and the metallic outer portion at every point of contact between the metallic inner portion and the metallic outer portion.

28. The composite medical device of claim 1 wherein the segment removed is in the shape of a spiral or helix.

29. A composite medical device comprising:
   a metallic composite elongate shaft including a metallic outer portion comprising a first metallic material co-drawn or co-extruded about a metallic inner portion including a lumen defined therein such that the metallic inner portion and the metallic outer portion are formed together as one unitary construction, the metallic inner portion comprising a second metallic material different from the first material, wherein the second metallic material is more flexible than the first metallic material, and wherein the composite elongate shaft has a distal region and a proximal region; and
   the distal region of the shaft has a segment of the metallic outer portion removed from the composite shaft to expose a segment of the metallic inner portion, wherein the distal region of the shaft is more flexible than the proximal region of the shaft.

30. The composite medical device of claim 29, wherein the metallic inner portion comprises a nickel-titanium alloy.

31. The composite medical device of claim 29, wherein the metallic inner portion comprises beta titanium.

32. The composite medical device of claim 31, wherein the metallic outer portion comprises stainless steel, cobalt alloy, Elgiloy, MP35N, tantalum, tungsten or refractory metal.

33. The composite medical device of claim 29, wherein the metallic inner portion comprises a super-elastic nickel-titanium alloy.

34. The composite medical device of claim 29, wherein the metallic inner portion comprises a linear-elastic nickel-titanium alloy.

35. The composite medical device of claim 29, wherein the metallic inner portion comprises a hollow tube having a length, the lumen extending along the entire length.

36. The composite medical device of claim 29, wherein the metallic outer portion comprises stainless steel, cobalt alloy, Elgiloy, MP35N, tantalum, tungsten, or refractory metal.

37. The composite medical device of claim 29, wherein the composite medical device comprises a catheter.

38. The composite medical device of claim 29, wherein the composite medical device comprises a guide catheter.

39. The composite medical device of claim 29, wherein the metallic material of the inner portion has a modulus of elasticity that is less than the modulus of elasticity of the metallic material of the outer portion.

40. The composite medical device of claim 29, wherein the metallic material of the outer portion has higher torsional rigidity than the metallic material of the inner portion.

41. The composite medical device of claim 29, wherein the distal region of the shaft having the segment of the metallic outer portion removed from the composite shaft also includes a second segment of the metallic outer portion that remains on the composite shaft in a pattern.

42. A composite medical device comprising:
   a unitary metallic composite elongate shaft including a metallic outer portion comprising a first metallic material co-drawn or co-extruded about a metallic inner portion including a lumen defined therein, the metallic inner portion comprising a second metallic material different from the first material, wherein the second metallic material is more flexible than the first metallic material, and wherein the composite elongate shaft has a distal region and a proximal region;
   means for providing the distal region with a higher level of flexibility relative to the proximal region; and
   means for providing the proximal region with a higher level of stiffness relative to the distal region.

43. A composite medical device produced by a process comprising:
   constructing a metallic composite elongate shaft by co-drawing or co-extruding a metallic outer portion comprising a first metallic material about a metallic inner portion including a lumen therein such that the metallic inner portion and the metallic outer portion are formed together as one unitary construction, the metallic inner portion comprising a second metallic material different from the first material, wherein the second metallic material is more flexible than the first metallic material, and wherein the composite elongate shaft has a distal region and a proximal region;
   removing a segment of the metallic outer portion from the composite shaft to expose a segment of the metallic inner portion;
   wherein removing the segment of the metallic outer portion includes selectively removing part of the first metallic material to form a pattern of the first metallic material that remains on the shaft; and
   wherein the pattern is in the form of a helix or spiral, or a series of cells, squares, ovals, rectangles, triangles or circles along the length of a portion of the shaft.

44. A composite medical device comprising:
   a unitary metallic composite elongate shaft including a metallic outer portion comprising a first metallic material co-drawn or co-extruded about a metallic inner portion including a lumen defined therein, the metallic inner portion comprising a second metallic material different from the first material, wherein the second metallic material is more flexible than the first metallic material, and wherein the composite elongate shaft has a distal region and a proximal region;
   the distal region of the shaft has a segment of the metallic outer portion removed from the composite shaft to expose a segment of the metallic inner portion, wherein the distal region of the shaft is more flexible than the proximal region of the shaft;
   wherein the distal region of the shaft having the segment of the metallic outer portion removed from the composite shaft also includes a second segment of the metallic outer portion that remains on the composite shaft in a pattern; and
   wherein the second segment of the metallic outer portion that remains on the composite shaft is in the shape of a spiral or helix, a series of cells, squares, rectangles, ovals or circles along the length of a portion of the shaft.

* * * * *